United States Patent [19]

Wilkinson

[11] 4,364,394
[45] Dec. 21, 1982

[54] COMBINED SUMP DRAINAGE AND IRRIGATION DEVICE

[76] Inventor: Lawrence H. Wilkinson, 718 Encino Pl., NE., Albuquerque, N. Mex. 87102

[21] Appl. No.: 210,052

[22] Filed: Nov. 24, 1980

[51] Int. Cl.³ .................................. A61M 25/00
[52] U.S. Cl. .............................. 604/96; 128/241; 604/128; 604/35; 604/39
[58] Field of Search ............ 128/240, 241, 246, 276, 128/348–350, 2

[56] References Cited

U.S. PATENT DOCUMENTS

| | | | |
|---|---|---|---|
| 2,930,378 | 3/1960 | Buyers | 128/350 R |
| 3,771,527 | 11/1973 | Ruisi | 128/350 R |
| 3,902,492 | 9/1975 | Greenhalgh | 128/349 B |
| 3,999,554 | 12/1976 | Kim et al. | 128/350 R |
| 4,114,625 | 9/1978 | Onat | 128/349 B X |

Primary Examiner—Dalton L. Truluck
Attorney, Agent, or Firm—Harvey B. Jacobson

[57] ABSTRACT

An elongated flexible tube structure is provided defining a plurality of individual passages extending longitudinally therethrough. The passages include an air vent passage, a suction passage and a fluid injection passage and the passages include first end portions opening separately outwardly of one end portion of the tube structure. The other end portion of the tube structure defines an outer tubular jacket enclosing and defining the second end portion of the air vent passage. The second end portion of the injection and suction passages are defined by separate tube sections disposed in and extending longitudinally of the tubular jacket. The end of the tubular jacket remote from the aforementioned one end portion thereof has the corresponding end of the suction tube section anchored therein and the latter includes lateral suction openings formed therein opening outwardly into the interior of the tubular jacket. The tubular jacket includes longitudinally spaced lateral air vent openings formed therein and the fluid passage tube section includes a flexible free end portion extending outwardly through one of the air vent openings. Also, a longitudinal midportion of the tube structure includes an outer inflatable bladder surrounding the tube structure and an inflation passage extending longitudinally of the tube structure having a first end opening into the interior of the bladder and a second end opening outwardly of the aforementioned one end of the tube.

4 Claims, 8 Drawing Figures

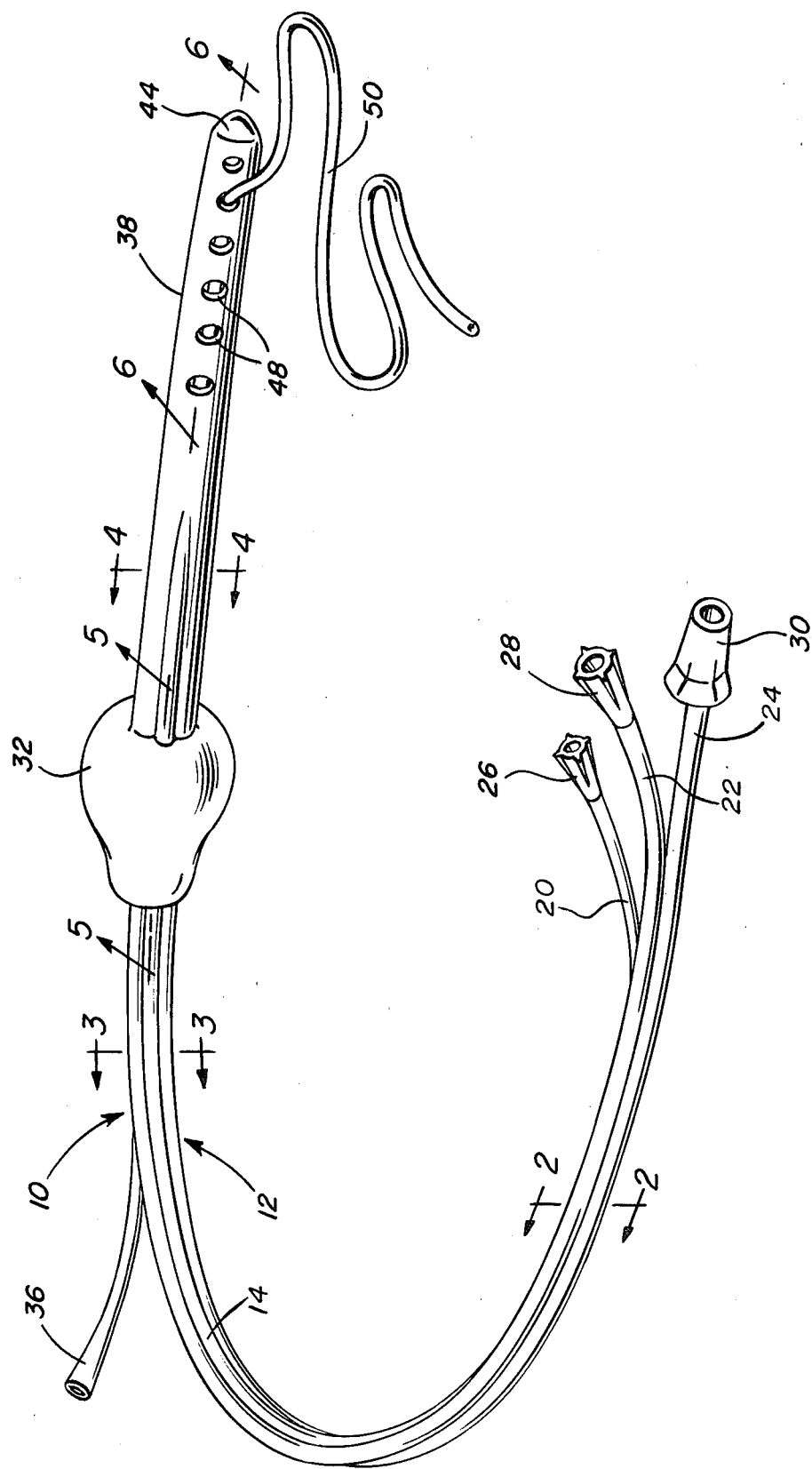

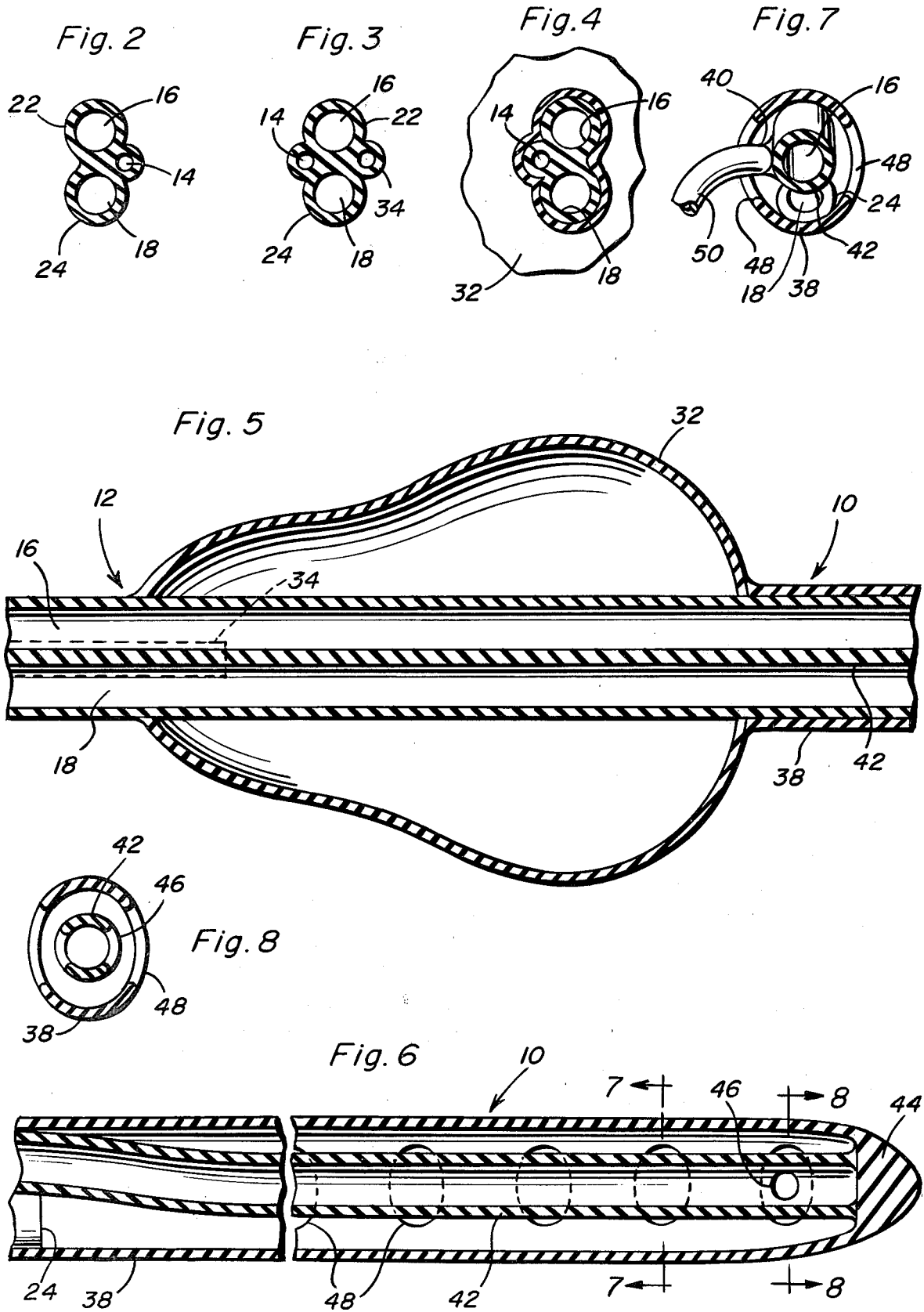

COMBINED SUMP DRAINAGE AND IRRIGATION DEVICE

BACKGROUND OF THE INVENTION

In numerous instances, it is desirable to reliably evacuate liquid, blood or exudate from the peritoneal cavity for a prolonged period of time. Various different structure heretofore have been provided for this purpose. Some of these structures as well as other similar structures are disclosed in U.S. Pat. Nos. 2,802,466, 3,394,705, 3,583,404, 3,902,492, 3,929,126, 3,999,554 and 4,057,065. However, some of the previously known devices for evacuating a peritoneal cavity include structure which is difficult to maintain in a sterile condition and irrigation through such previously known devices is difficult to satisfactorily achieve and maintain. Further, drainage openings in previously known device become occluded with clots, purulent or proteinaceous material. In addition, suction provided to these previously known device tends to pull surrounding tissue into the drain openings thereof preventing the escape of accumulations desired to be drained from the peritoneal cavity. Further, irrigation attempts with previously known devices often result in leakage around the device exit site.

Accordingly, a need exists for an apparatus whereby liquids, blood or exudate may be effectively evacuated from the peritoneal cavity for prolonged periods.

BRIEF DESCRIPTION OF THE INVENTION

The drainage and irrigation device of the instant invention has been specifically designed to be readily insertable through the abdominal wall into the peritoneal cavity and to be efficient in obtaining and maintaining irrigation, drainage and to allow for fluid injection with an apparatus facilitating the maintenance of sterility.

The main object of this invention is to provide a sump drainage and irrigation device through the usage of which irrigation may be readily obtained and maintained.

Another object of this invention is to provide a device in accordance with the preceding object and constructed in a manner such that sterility maintenance will be possible with reasonable assurance.

Another important object of this invention is to provide a drainage and irrigation device constructed in a manner to lessen the tendency of the drainage opening thereof to become occluded with clots, purulent or proteinaceous material.

Yet another object of this invention is to provide an apparatus in accordance with the preceding objects and which will lessen the tendency of surrounding tissue to be drawn into the inlet end of the device as a result of suction being applied to the outlet end thereof.

A final object of this invention to be specifically enumerated herein is to provide a drainage and irrigation device in accordance with the preceding objects and which will conform to conventional forms of manufacture be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the drainage and irrigation device of the instant invention;

FIG. 2 is an enlarged sectional view taken substantially upon the plane indicated by the section line 2—2 of FIG. 1;

FIG. 3 is an enlarged sectional view taken substantially upon the plane indicated by the section line 3—3 of FIG. 1;

FIG. 4 is an enlarged sectional view taken substantially upon the plane indicated by the section line 4—4 of FIG. 1;

FIG. 5 is an enlarged fragmentary longitudinal vertical sectional view taken substantially upon the plane indicated by the section line 5—5 of FIG. 1;

FIG. 6 is an enlarged fragmentary longitudinal vertical sectional view taken substantially upon the plane indicated by the section line 6—6 of FIG. 1;

FIG. 7 is a transverse sectional view taken substantially upon the plane indicated by the section line 7—7 of FIG. 6; and FIG. 8 is a transverse sectional view taken substantially upon the plane indicted by the section line 8—8 of FIG. 6.

DETAILED DESCRIPTION OF THE INVENTION

Referring now more specifically to the drawings, the numeral 10 generally designates the drainage and irrigation device of the instant invention. The device 10 comprises an elongated flexible tube structure referred to in general by the reference numeral 12 and the tube structure 12 defines a plurality of individual passages 14, 16 and 18 extending longitudinally therethrough. The passage 14 comprises an injection passage, the passage 16 comprises a suction passage and the passage 18 comprises a vent passage 18. A first set of ends of the injection, suction and vent passages 14, 16 and 18 open separately outwardly of the tube structure 12 as at 20, 22 and 24, respectively, and include adapter end portions 26, 28 and 30 for removable connection to a vent discharge assembly (not shown), a source of vacuum (not shown) and a source of injection fluid (not shown) under pressure.

The tube structure 12 also includes an outer inflatable bladder 32 surrounding the tube structure 12 and the latter additionally includes an inflation passage 34 extending longitudinally of the tube section and opening into the bladder 32 at one end. The bladder 32 is disposed centrally intermediate the opposite ends of the tube structure 12 and the end of the inflation passage 34 remote from bladder 32 opens outwardly of the tube structure 12 as at 36 for operative communication with a source (not shown) of fluid under pressure for inflating the bladder 32.

The end portion of the tube structure 12 on the side of the bladder 32 remote from the adapter end portions 26, 28 and 30 defines an outer tubular jacket 38 enclosing and defining the corresponding end of the air vent passage 18. Corresponding end portions of the injection and suction passages 14 and 16 are defined by separate tube sections 40 and 42, respectively, enclosed within the outer jacket 38 and extending longitudinally thereof. The end of the tube section 42 remote from the bladder 32 includes an end wall 44 integral with the corresponding end of the outer tubular jacket 38 and a plurality of radial bores 46 opening outwardly of the interior of the tube section 42 into the interior of the tubular jacket 38. In addition, the outer tubular jacket 38 includes a plurality of longitudinally spaced radial bores or openings 48 of varying size.

The tube section 40 extends along and is anchored relative to the tube section 42 at a point spaced from the end wall 44 and includes a flexible free end portion 50 which extends outwardly through and considerably beyond one of the openings 48.

It will be noted that the effective cross-sectional area of the interior of the outer tubular jacket 38 comprising the air vent is greater than the effective cross-sectional area of the suction tube section 42. Further, the openings 48 are considerably larger in diameter than the openings or bores 46 and the bladder 32 is structured in a manner whereby inflation thereof at the level of peritoneum prevents the device 10 from being accidentally withdrawn and also the escape of irrigation liquid. The bladder 32 is tapered toward the outer end of the tube section 12 for this purpose.

The air vent passage adapter 30 opens outwardly of the tube section 12 at least 50 cm. from the bladder 32 and thereby escapes contamination from bed linen. An appropriate guard may be applied over the inflow end of the air vent passage 18 by the adapter 30.

In operation, the end of the tube structure 10 having the outer jacket 38 thereon may be placed within a patient's peritoneal cavity in a manner such that the face end portion 50 of tube section 40 of injection passage 14 is positioned as desired for subsequent injection of irrigation fluids and/or proteolytic agents. The bladder 32 may be positioned immediately inward of the incision and subsequently inflated as desired through inflation passage 34 in order to prevent accidental withdrawal of the tube structure 10. Thereafter, suction may be suitably applied to the suction passage 16 through the adapter 28 and suitable irrigation fluids as well as proteolytic agents may be injected into the peritoneal cavity through passage 14, the passage 18 serving as a vent passage.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A combined sump drainage and irrigation device including an elongated flexible tube structure defining a pair of side-by-side large diameter individual suction and vent passages and pair of small diameter individual inflation and injection passages disposed on remote sides of adjacent portions of said large diameter passages, an inflatable elongated balloon bladder surrounding said tube structure centrally intermediate its opposite ends, extending longitudinally thereof and sealed at its opposite ends to longitudinally spaced portions of said tube structure, one set of ends of said large diameter passages and one of said small diameter passages opening separately outwardly of one end portion of said tube structure, the other end of one of said small diameter passages opening outwardly into the interior of said bladder, said tube structure including a tubular jacket enclosing the other end portion of said tube structure and having a first end adjacent said bladder sealed relative to the outer surfaces of said tube structure and an end wall closing the second end of said jacket remote from said bladder, the other end of said vent passage terminating a spaced distance from said end wall and opening into the interior of said jacket, said other end of said suction passage opening into one end of a tube section disposed in and extending centrally longitudinally of said jacket and having its other end anchored to and closed by said end wall, said jacket including longitudinally spaced lateral air vent openings formed therein intermediate said end wall and said first end of said jacket, said tube section other end including lateral openings formed therein spaced from but adjacent said end wall, the other end of said injection passage opening into one end portion of a second flexible tube section loosely received in and extending longitudinally of said jacket and having its other end portion directed outwardly through one of said air vent openings and extending outwardly beyond said one air vent opening.

2. The device of claim 1 wherein said one end of said inflation passage opens separately outwardly of said tube structure intermediate said bladder and said one set of ends of said large diameter passages.

3. The device of claim 1 wherein said one set of ends of said large diameter passages and corresponding end of the other small diameter passage include adapter end portions thereon for removable connection to a vent discharge assembly, a source of vacuum and a source of injection fluid under pressure.

4. The device of claim 1 wherein said inflatable bladder tapers toward said one end portion of said tube structure.

* * * * *